United States Patent [19]

Seto et al.

[11] Patent Number: 4,879,400

[45] Date of Patent: Nov. 7, 1989

[54] PROCESS FOR PRODUCING ALPHA-(BENZYLIDENE)ACETONYLPHOSPHONATES

[75] Inventors: Kiyotomo Seto; Hiroo Matsumoto; Ryozo Sakoda, all of Funabashi, Japan

[73] Assignee: Nissan Chemical Industries Ltd., Tokyo, Japan

[21] Appl. No.: 145,042

[22] Filed: Jan. 19, 1988

[30] Foreign Application Priority Data

Jan. 21, 1987 [JP] Japan .............................. 62-011752

[51] Int. Cl.$^4$ ............................................. C07F 9/21
[52] U.S. Cl. .................................... 558/83; 558/142; 558/178
[58] Field of Search ........................ 558/142, 178, 83

[56] References Cited

U.S. PATENT DOCUMENTS 3,047,606 7/1962 Wadsworth, Jr. .................. 558/142

OTHER PUBLICATIONS

Moita et al., "Bull Pharm Bull Tokyo", 35(9), (1987), 3898–904, abstract in ICI, vol. 109, Issue 1274, (1988).

Primary Examiner—Anton H. Sutto
Attorney, Agent, or Firm—Oblon, Spivak, McClelland, Maier & Neustadt

[57] ABSTRACT

A process for producing an α-(benzylidene)acetonylphosphonate of the formula:

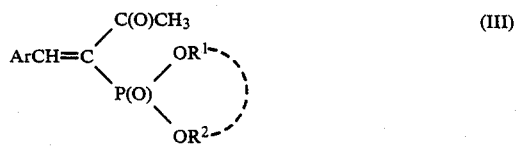

wherein Ar is phenyl substituted by at least one substituent selected from the group consisting of fluorine, chlorine, bromine, nitro, chloromethyl, dichloromethyl, trichloromethyl, trifluoromethyl, —CO$_2$R$^7$ wherein R$^7$ is C$_1$–C$_5$ alkyl, —CONR$^7$R$^8$ wherein R$^7$ is as defined above and R$^8$ is C$_1$–C$_5$ alkyl, —C(O)R$^7$ wherein R$^7$ is as defined above, —OC(O)R$^7$ wherein R$^7$ is as defined above, —OSO$_3$R$^7$ wherein R$^7$ is as defined above, —OCF$_3$, —S(=O)$_2$R$^7$ wherein R$^7$ is as defined above, —CN and —SO$_3$R$^7$ wherein R$^7$ is as defined above, and each of R$^1$ and R$^2$ which may be the same or different is a saturated or unsaturated C$_1$–C$_{12}$ aliphatic group, or R$^1$ and R$^2$ together form 1,2-ethylene, 1,3-propylene or 1,4-butylene, which is unsubstituted or substituted by from one to four C$_1$–C$_3$ alkyl groups, which comprises:

(a) reacting an aldehyde of the formula:

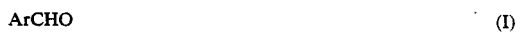

wherein Ar is as defined above, with an acetonylphosphonate of the formula:

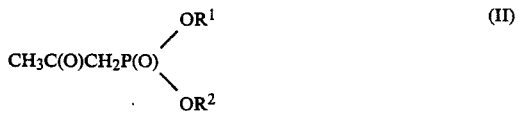

wherein R$^1$ and R$^2$ are as defined above, in the presence of a secondary amine of the formula:

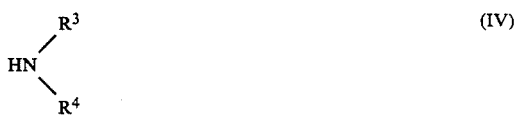

wherein each of R$^3$ and R$^4$ which may be the same or different is C$_1$–C$_4$ alkyl, or R$_3$ and R$_4$ together form 1,4-butylene or 1,5-pentylene, which is unsubstituted or substituted by from one to four C$_1$–C$_2$ alkyl groups, —CH$_2$CH$_2$OCH$_2$CH$_2$— or —CH$_2$CH$_2$NHCH$_2$CH$_2$—, and an α-halogeno fatty acid of the formula:

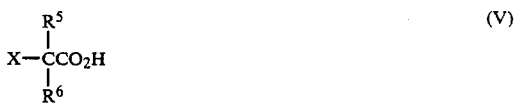

wherein X is fluorine, chlorine, bromine or iodine, and each of R$^5$ and R$^6$ which may be the same or different is hydrogen, fluorine, chlorine, bromine, iodine or C$_1$–C$_4$ alkyl; or (b) reacting a compound of the formula

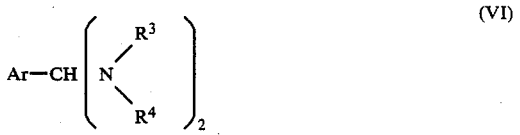

wherein Ar, R$^1$ and R$^2$ are as defined above, with an acetonylphosphonate of the formula II as defined above, in the presence of an α-halogeno fatty acid of the formula V as defined above.

7 Claims, No Drawings

PROCESS FOR PRODUCING ALPHA-(BENZYLIDENE)ACETONYLPHOSPHONATES

The present invention relates to a process for producing α-(benzylidene)acetonylphosphonates. The α-(benzylidene)acetonylphosphonate derivatives prepared by the present invention are useful as intermediates for poly substituted phosphonate derivatives (F. BARBOT, E. PARAISO and Ph. MIGINIAC, Tetrahedron Lett., 25 (39), 4369-4370 (1984)), as intermediates for the preparation of conjugated dienes (J. M. McIntosh and R. A. Sieler, Can. J. Chem., 56, 226-231 (1977)) or as intermediates for medicines (Japanese Unexamined Patent Publications No. 161392/1984, No. 69089/1985, No. 248693/1985, No. 258194/1985, No. 030591/1986, No. 63688/1986 and No. 63689/1986).

The reaction of an acetonylphosphonate with an aromatic aldehyde was first reported by Pudovik et al (A. N. Pudovik, G. E. Yastrebova and V. I. Nikitina, Zh. Obsh. Khim., 37 (2), 510-511 (1967)). They conducted the condensation reaction of benzaldehyde with diethyl acetonylphosphonate in the presence of a piperidine catalyst to obtain α-(benzylidene)acetonylphosphonate in a yield of 64.7%, as represented by the following scheme 1.

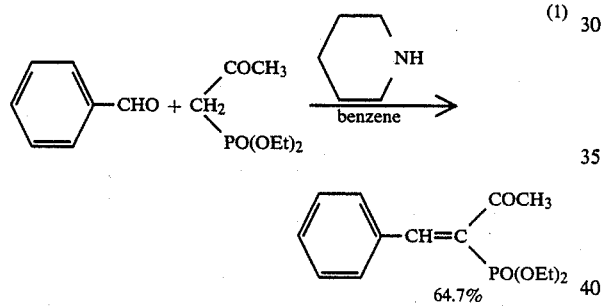

However, it is reported that when the aromatic ring is substituted by an electron attracting group, a dephosphonation reaction called Horner-Emmons reaction proceeds preferentially, whereby the desired phosphonate derivative is hardly obtainable (S. Patai and A. Schwartz, J. Org. Chem., 25, 1232-1234 (1960)). The present inventors have conducted the reaction under the same condition as in the scheme 1 and have confirmed that the Horner-Emmons reaction proceeds preferentially (see the scheme 2 and Comparative Example 2).

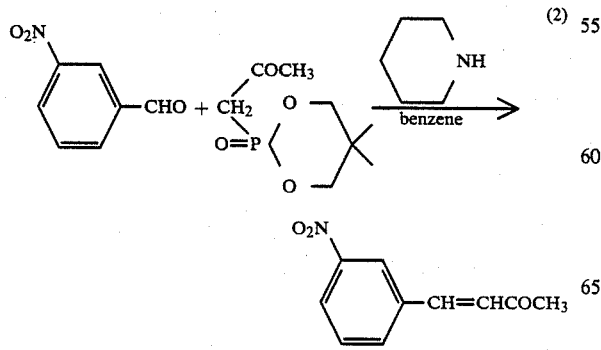

Patai et al discovered that good results could be obtained when piperidine-acetic acid was used as a catalyst for the condensation of an aromatic aldehyde with α-methylene phosphonate (S. Patai and A. Schwartz, J. Org. Chem., 25, 1232-1234 (1960)). Since then, this method has been widely employed (scheme 3).

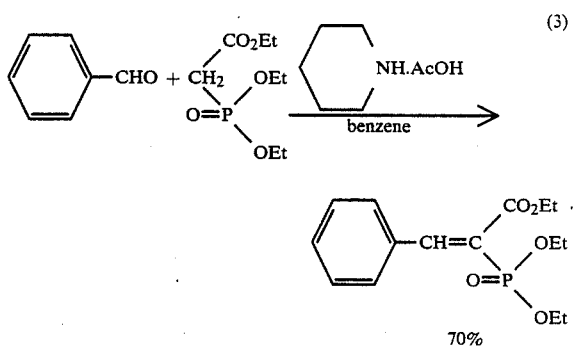

Many α-(benzylidene)acetonylphosphonate derivatives have been synthesized by using this method (Japanese Unexamined Patent Publications No. 161392/1984 and No. 248693/1985). However, the yield is very low particularly when an aromatic aldehyde is substituted by a strong electron attractive group such as a $NO_2$ group. According to the research by the present inventors, this is caused by the Horner-Emmons reaction which produces a methyl styryl ketone derivative of the formula:

$$Ar^a-CH=CHCOCH_3 \qquad (a)$$

wherein $Ar^a$ is phenyl substituted by an electron attractive group, as a by-product as well as a compound of the formula:

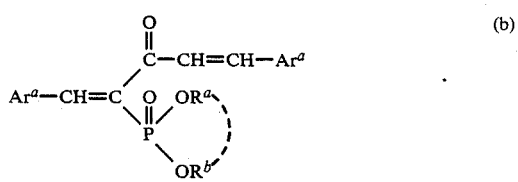

wherein $Ar^a$ is as defined above, and each of $R^a$ and $R^b$ which may be the same or different is alkyl, or $R^a$ and $R^b$ together form alkylene and a compound of the formula:

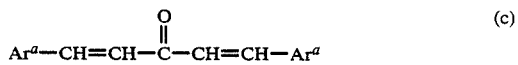

wherein $Ar^a$ is as defined above, as by-products.

Thus, even if an acetonylphosphonate of formula:

wherein $R^a$ and $R^b$ are as defined above is reacted with a substituted benzaldehyde of the formula:

$$Ar^aCHO \qquad (e)$$

wherein Ar$^a$ is as defined above, in accordance with the conventional methods, the yield of an α-(benzylidene)acetonylphosphonate derivative of the formula:

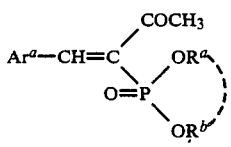   (f)

wherein Ar$^a$, R$^a$ and R$^b$ are as defined above, is low.

It is an object of the present invention to improve the yield for the preparation of an α-(benzylidene)acetonylphosphonate derivative of the formula (f) by reacting a substituted benzaldehyde of the formula (e) with an acetonylphosphonate of the formula (d).

The present invention provides a process for producing an α-(benzylidene)acetonylphosphonate of the formula:

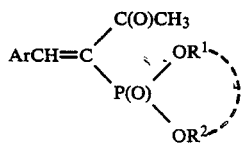   (III)

wherein Ar is phenyl substituted by at least one substituent selected from the group consisting of fluorine, chlorine, bromine, nitro, chloromethyl, dichloromethyl, trichloromethyl, trifluoromethyl, —CO$_2$R$^7$ wherein R$^7$ is C$_1$–C$_5$ alkyl, —CONR$^7$R$^8$ wherein R$^7$ is as defined above and R$^8$ is C$_1$–C$_5$ alkyl, —C(O)R$^7$ wherein R$^7$ is as defined above, —OC(O)R$^7$ wherein R$^7$ is as defined above, —OSO$_3$R$^7$ wherein R$^7$ is as defined above, —OCF$_3$, —S(=O)$_2$R$^7$ wherein R$^7$ is as defind above, —CN and —SO$_3$R$^7$ wherein R$^7$ is as defined above, and each of R$^1$ and R$^2$ which may be the same or different is a saturated or unsaturated C$_1$–C$_2$ aliphatic group, or R$^1$ and R$^2$ together form 1,2-ethylene, 1,3-propylene or 1,4-butylene, which is unsubstituted or substituted by from one to four C$_1$–C$_3$ alkyl groups, which comprises:

(a) reacting an aldehyde of the formula:

ArCHO   (I)

wherein Ar is as defined above, with an acetonylphosphonate of the formula:

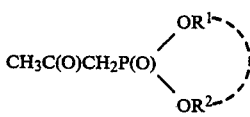   (II)

wherein R$^1$ and R$^2$ are as defined above, in the presence of a secondary amine of the formula:

   (IV)

wherein each of R$^3$ and R$^4$ which may be the same or different is C$_1$–C$_4$ alkyl, or R$_3$ and R$_4$ together form 1,4-butylene or 1,5-pentylene, which is unsubstituted or substituted by one to four C$_1$–C$_2$ alkyl groups, —CH$_2$CH$_2$OCH$_2$CH$_2$— or —CH$_2$CH$_2$NHCH$_2$CH$_2$—, and an α-halogeno fatty acid of the formula:

   (V)

wherein X is fluorine, chlorine, bromine or iodine, and each of R$^5$ and R$^6$ which may be the same or different is hydrogen, fluorine, chlorine, bromine, iodine, C$_1$–C$_4$ alkyl; or (b) reacting a compound of the formula:

   (VI)

wherein Ar, R$^1$ and R$^2$ are as defined above, with an acetonylphosphonate of the formula II as defined above, in the presence of an α-halogeno fatty acid of the formula V as defined above.

Namely, by the reaction (a) or (b), the α-(benzylidene)acetonylphosphonate derivative of the formula III can be obtained in high yield.

Further, the present inventors have found that the α-(benzylidene)acetonylphosphonate can be obtained in high yield also by forming an aminal of the formula VI from a secondary amine of the formula IV and a substituted benzaldehyde of the formula I and reacting the reaction solution containing the aminal with an acetonylphosphonate of the formula II in the presence of an α-halogeno fatty acid of the formula V in the same reaction solution.

The aminal of the formula VI is a known compound, which can be prepared by a known method (e.g. M. Sekiya and H. Sakai, Chem. Pharm. Bull., 17 (1), 32–35 (1969)). The temperature for the reaction for the preparation of an α-(benzylidene)acetonylphosphonate of the formula III is within a range of from cooling with ice to the reflux temperature of the solvent, preferably within a range of from cooling with ice to 100° C.

The molar ratios of the respective compounds used for the synthesis according to the present invention are as follows.

Namely, the molar ratios of the compounds of the formulas I, II, IV and V are I:II:IV:V=0.8–1.2:0-.8–1.2:0.01–2.4:0.01–2.4, preferably I:II:IV:V=0.-95–1.05:0.95–1.05:0.1–2.0:0.1–2.0.

Further, the molar ratios of the compounds of the formulas II, V and VI are II:V:VI=0.8–1.2:1.6–2.4:0-.8–1.2, preferably II:V:VI=0.95–1.05:1.9–2.1:0.95–1.05.

As the reaction solvent, an ether solvent such as THF (tetrahydrofuran), an amide solvent such as DMF (dimethylformamide), DMA (dimethylacetamide) or N-methylpyrrolidone, a halogenoalkane solvent such as dichloromethane or chloroform, a sulfoxide solvent such as DMSO (dimethylsulfoxide) a nitrile solvent such as acetonitrile, an aromatic hydrocarbon solvent such as benzene, toluene or xylene, or an ester solvent such as ethyl acetate, can be used. Among these solvents, preferred solvents include toluene, benzene, tetrahydrofuran, acetonitrile and chloroform. Particularly preferred solvents are toluene and benzene.

Now, the present invention will be described in further detail with reference to Reference Examples, Comparative Examples and Working Examples. However, it should be understood that the present invention is by no means restricted by these specific Examples.

REFERENCE EXAMPLE 1

5.31 g (50.0 mmol) of benzaldehyde was dissolved in 30 ml of benzene, and 5.80 g of boric anhydride powder was suspended therein. Then, 10.5 g (121 mmol) of morpholine was added thereto under stirring. After the heat generation ceased, the mixture was heated again and reacted at 50° C. for two hours. The reaction mixture was cooled to room temperature and subjected to filtration under suction to remove solid substance. The solvent was distilled off from the filtrate. The residue thus obtained (oily under heating) was dissolved in 40 ml of isopropyl ether, and the solution was gradually cooled and then left to stand overnight in a refrigerator, whereby 11.02 g (yield: 84%) of desired aminal was obtained as colorless crystals having a melting point of from 102° to 103° C.

REFERENCE EXAMPLES 2 TO 5

In the same manner as in Reference Example 1, the following aminals were prepared. The reaction scheme is represented as follows:

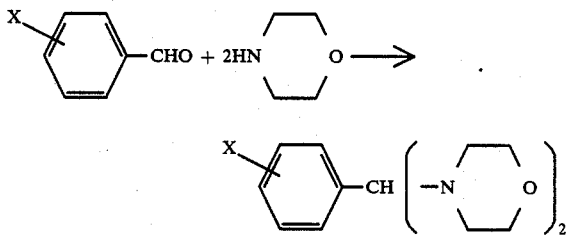

| Reference Example No. | X | Yield (%) | Melting point (°C.) | Solvent for precipitation |
| --- | --- | --- | --- | --- |
| 2 | p-Cl | 90 | 133–137 | Isopropyl ether |
| 3 | p-NO$_2$ | 64 | Decomposed at 180–182 | Benzene |
| 4 | m-NO$_2$ | 73 | 134–135 | Isopropyl ether |
| 5 | o-NO$_2$ | 92 | 125–129 | Isopropyl ether |

EXAMPLE 1

2.62 g (10.0 mmol) of 1,1'-benzylidene dimorpholine was dissolved in 20.0 g of toluene, and 2.28 g (20.0 mmol) of trifluoroacetic acid was dropwise added thereto under stirring. After the completion of the dropwise addition, the mixture was heated to 60° C., and 15 minutes later, 2.06 g (10.0 mmol) of 2,2-dimethylpropylene acetonylphosphonate was added and dissolved therein. After confirming the dissolution, the warm bath was taken off. While the mixture was left to cool, the reaction was continued for 30 minutes to complete the reaction. The reaction mixture was cooled with ice, and 20.0 g of cold water was added thereto to dissolve a trifluoroacetate of morpholine. Then, the mixture was subjected to liquid separation, and toluene layer was taken and dried over anhydrous sodium sulfate. Then, the solvent was distilled off. 2.49 g of a slightly yellow residue thus obtained was purified by column chromatography (silica gel: 200 g, ethyl acetate/benzene=1/1) to obtain 2.04 g (yield: 69%) of desired 2,2-dimethylpropylene α-(benzylidene)acetonylphosphonate as a slightly yellow oily substance. (This oily substance was crystallized when left to stand at room temperature for three days.) From the NMR analysis, this substance was found to be a mixture of E-isomer/Z-isomer=80/20.

NMR(CDCl$_3$)δ(ppm): 0.73(s), 1.06(s), 1.11(s), 1.21(s), total 6H; 2.24(s), 2.5(s), total 3H; 3.4–4.5(m), 4H; 6.7–7.7(m), 5H; 7.80(s), 8.29(s), total 1H.

EXAMPLE 2

In the same manner as in Example 1, 2,2-dimethylpropylene α-(benzylidene)acetonylphosphonate (a compound of the formula III wherein R$^1$ and R$^2$ together form —CH$_2$C(CH$_3$)$_2$CH$_2$— and Ar is p-chlorophenyl) was prepared by using 1,1'-(p-chlorobenzylidene)-dimorpholine instead of 1,1'-benzylidene dimorpholine.

Yield: 85%
NMR integral ratio: E/Z=80/20
NMR(CDCl$_3$)δ(ppm): 0.77(s), 1.07(s), 1.13(s), 1.24(s), total 6H; 2.28(s), 2.56(s) total 3H; 3.3–4.5(m), 4H; 6.6–8.5(m), 5H.

EXAMPLE 3

3.07 g (10.0 mmol) of 1,1'-(p-nitrobenzylidene)dimorpholine was suspended in 20.0 g of toluene, and 2.28 g (20.0 mmol) of trifluoroacetic acid was dropwise added thereto under stirring. After the completion of the dropwise addition, the mixture was heated to 60° C., and 15 minutes later, 2.06 g (10.0 mmol) of 2,2-dimethylpropylene acetonylphosphonate was added and dissolved therein. After confirming the dissolution, the warm bath was removed, and while the mixture was left to cool, the reaction was continued for 30 minutes to complete the reaction. This reaction mixture was cooled with water, and 20.0 g of cold water was added thereto for precipitation to obtain 2.82 g (yield: 83%) of desired 2,2-dimethylpropylene α-(p-nitrobenzylidene)acetonylphosphonate (Compound of the formula III, wherein R$^1$ and R$^2$ together form —CH$_2$C(CH$_3$)$_2$CH$_2$— and Ar is p-nitrophenyl) as substantially colorless crystals. From the NMR analysis, this substance was found to be a mixture of E-isomer/Z-isomer=95/5.

NMR of E-isomer (CDCl$_3$)δ(ppm) 1.07(s, 3H), 1.17(s, 3H), 2.31(s, 3H), 3.2–4.6(m, 4H), 7.1–8.6(m, 5H)

EXAMPLES 4 AND 5

By using 1,1'-(m-nitrobenzylidene(dimorpholine or 1,1'-(o-nitrobenzylidene)dimorpholine instead of 1,1'-(p-nitrobenzylidene)dimorpholine, the corresponding α-substituted (benzylidene)acetonylphosphonate derivative was prepared in the same manner as in Example 3. However, as is different from Example 3, recovery of the recovery was conducted also from the mother liquor for precipitation by means of column chromatography (silica gel, ethyl acetate).

The test results are shown in the following Table.

| Example No. | Substituent | Yield (%) | E/Z (NMR integral ratio) | NMR(CDCl$_3$) δ-value |
| --- | --- | --- | --- | --- |
| 4 | m-NO$_2$ | 90 | 95:5 | E-isomer 1.07(s, 3H), 1.19(s, 3H) 2.33(s, 3H), 3.2–4.6(m, 4H), 7.0–8.6(m, 5H) |

| Example No. | Substituent | Yield (%) | E/Z (NMR integral ratio) | NMR(CDCl₃) δ-value |
|---|---|---|---|---|
| 5 | o-NO₂ | 57 | 30:70 | 0.82(s), 1.02(s), 1.17(s), 1.30(s), total 6H; 2.28(s), 2.58(s), total 3H; 3.3–4.4(m, 4H), 6.8–8.9(m, 5H) |

EXAMPLE 6

15.1 g of m-nitrobenzaldehyde and 17.0 g of piperidine were dissolved in 200 g of benzene, and the mixture was refluxed for 3 hours. Water formed as the reaction proceeded, was removed azeotropically. The reaction solution was cooled with ice, and 22.8 g of trifluoroacetic acid was dropwise added thereto. The mixture was stirred for 30 minutes under cooling with ice. Then, 20.6 g of 2,2-dimethylpropylene acetonylphosphonate was added, and the reaction solution was heated to 50° C. and maintained at that temperature for 30 minutes, and then cooled again with ice. The formed crystals were collected by filtration and dried to obtain 22.0 g of desired 2,2-dimethylpropylene α-(m-nitrobenzylidene)acetonylphosphonate. The filtrate was washed twice with 75 g of water and cooled with ice, whereby 6.0 g (dry weight) of crystals of the desired product was further obtained.

Yield: 83%, mp: 148°–149° C.

EXAMPLE 7

10.3 g of 2,2-dimethylpropylene acetonylphosphonate and 7.55 g of m-nitrobenzaldehyde were dissolved in 100 ml of toluene. Then, 5.7 g of trifluoroacetic acid and 4.25 g of piperidine were added thereto, and the mixture was subjected to azeotropic water removal for two hours. The reaction solution was cooled with ice for 2 hours, and precipitated crystals were removed by filtration. The filtrate was washed with 50 ml of water. The toluene solution was left to stand at 0° C. for 10 hours to obtain 9.2 g (yield: 54%) of desired 2,2-dimethylpropylene α-(m-nitrobenzylidene)acetonylphosphonate as crystals.

EXAMPLE 8

A mixture comprising 302 g (2.00 mol) of m-nitrobenzaldehyde, 348 g (4.00 mol) of morpholine and 200 g of benzene was refluxed for 4.5 hours while removing water azeotropically. The solution thereby obtained was cooled to 30° C. with water, and then 378 g (4.00 mol) of monochloroacetic acid was added thereto. The mixture was stirred for 30 minutes under cooling with water. Then, the mixture was heated again to an internal temperature of 60° C., and 412 g (2.00 mol) of 2,2-dimethylpropylene acetonylphosphonate was added thereto. The mixture was reacted for 1 hour. After the completion of the reaction, the reaction mixture was extracted with 1,400 g of warm water of 60° C. while the mixture was still hot, to remove the monochloroacetate of morpholine. The benzene layer was collected, and 800 g of benzene was distilled off. Then, precipitation was conducted under cooling with ice to obtain 428 g (yield: 63%) of desired α-(m-nitrobenzylidene)acetonylphosphonate.

EXAMPLE 9

1.78 g of propylene acetonylphosphonate was suspended in 12 g of toluene, and 1.84 g of monochloroacetic acid was added and dissolved therein under stirring. After confirming the dissolution, 2.83 g of 1,1'-(o-nitrobenzylidene)dimorpholine was added thereto, and the mixture was stirred at about 20° C. for 2 hours. The reaction mixture was cooled with ice and 10 g of cold water was added thereto for precipitation to obtain 2.0 g (yield: 64.2%) of desired propylene α-(o-nitrobenzylidene)acetonylphosphonate as white crystals. From the NMR analysis, this product was found to be a mixture of E-isomer/Z-isomer=26/7.

COMPARATIVE EXAMPLE 1

(Conventional method: in the coexistence of piperidine and acetic acid)

1.9 g of 2,2-dimethylpropylene acetonylphosphonate and 1.5 g of m-nitrobenzaldehyde were dissolved in 2 ml of benzene, and 0.5 ml of piperidine and two drops of acetic acid were added. The mixture was refluxed for 3 hours to remove water azeotropically. After cooling, the reaction solution was subjected to silica gel chromatography (eluate: ethyl acetate/methanol=9/1 (v/v), Rf: 0.7) to obtain 0.99 g (yield: 31%) of desired 2,2-dimethylpropylene α-(m-nitrobenzylidene)acetonylphosphonate.

COMPARATIVE EXAMPLE 2

(In the presence of piperidine)

1.9 g of 2,2-dimethylpropylene acetonylphosphonate and 1.5 g of m-nitrobenzaldehyde were dissolved in 2 ml of benzene, and 0.5 ml of piperidine was added thereto. The mixture was refluxed for 1.5 hours to remove water azeotropically. After cooling, the reaction solution was subjected to a silica gel chromatography (eluate: ethyl acetate/methanol=9/1 (v/v), Rf: 0.7) to obtain 1.15 g (yield: 36% of desired 2,2-dimethylpropylene α-(m-nitrobenzylidene)-acetonylphosphonate.

COMPARATIVE EXAMPLE 3

(In the presence of piperidine)

1 g of 2,2-dimethylpropylene acetonylphosphonate and 0.75 g of m-nitrobenzaldehyde or dissolved in 10 ml of benzene, and 1 g of piperidine was added thereto. The mixture was stirred at room temperature for 24 hours. This reaction solution was analyzed by high performance liquid chromatography (ODS reverse column, eluate: methanol/water=3/2 (v/v), UV (254 nm) detection), whereby methyl(m-nitrostyryl)ketone was detected excusively as a product of the Horner-Emmons reaction.

COMPARATIVE EXAMPLE 4

(In the absence of a secondary amine) 0.515 g of 2,2-dimethylpropylene acetonylphosphonate and 0.38 g of m-nitrobenzaldehyde were dissolved in 5 ml of benzene, and 0.1 ml of trifluoroacetic acid was added thereto. The mixture was refluxed for one hour, but the reaction did not proceed at all.

The results of this experiment show that the addition of a secondary amine of the formula IV is essential for the reaction to proceed properly.

We claim:

1. A process for producing an α-(benzylidene)acetonylphosphonate of the formula:

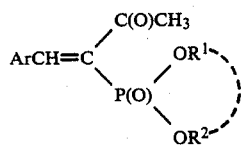

wherein Ar is a phenyl group substituted by at least one substituent selected from the group consisting of fluorine, chlorine, bromine, nitro, chloromethyl, dichloromethyl, trichloromethyl, trifluoromethyl, $-CO_2R^7$ wherein $R^7$ is $C_1-C_5$ alkyl, $-CONR^7R^8$ wherein $R^7$ is as defined above and $R^8$ is $C_1-C_5$ alkyl, $-C(O)R^7$ wherein $R^7$ is as defined above, $-OC(O)R^7$ wherein $R^7$ is as defined above, $-OSO_3R^7$ wherein $R^7$ is as defined above, $-OCF_3$, $-S(=O)_2R^7$ wherein $R^7$ is as defined above, $-CN$ and $-SO_3R^7$ wherein $R^7$ is as defined above, and each or $R^1$ and $R^2$, which are the same or different, is a saturated or unsaturated $C_1-C_{12}$ aliphatic group, or $R^1$ and $R^2$ together form 1,2-ethylene, 1,3-propylene or 1,4-butylene, which is unsubstituted or substituted by from one to four $C_1-C_3$ alkyl groups, which comprises:

(a) reacting an aldehyde of the formula:

ArCHO                               (I)

wherein Ar is as defined above, with an acetonylphosphonate of the formula:

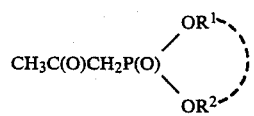

wherein $R^1$ and $R^2$ are as defined above, in the presence of a secondary amine of the formula:

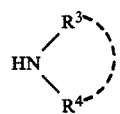

wherein each of $R^3$ and $R^4$, which are the same or different, is $C_1-C_4$ alkyl, or $R_3$ and $R_4$ together form 1,4-butylene or 1,5-pentylene, which is unsubstituted or substituted by from one to four $C_1-C_2$ alkyl groups, $-CH_2CH_2OCH_2CH_2-$ or $-CH_2CH_2NHCH_2CH_2-$, and an α-halogeno fatty acid of the formula:

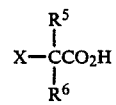

wherein X is fluorine, chlorine, bromine or iodine, and each of $R^5$ and $R^6$, which are the same or different, is hydrogen, fluorine, chlorine, bromine, iodine or $C_1-C_4$ alkyl; or (b) reacting a compound of the formula:

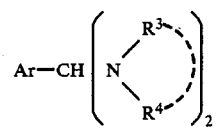

wherein Ar,'$R^1$ and $R^2$ are as defined above, with an acetonylphosphonate of the formula II as defined above, in the presence of an α-halogeno fatty acid of the formula V as defined above, and wherein the compounds of the formulas I, II, IV, V and VI are reacted in the following molar ratios: I:II:IV:V being 0.8-1.2:0-.8-1.2:0.01-2.4:0.01-2.4; and II:V:VI being 0.8-1.2:1-.6-2.4:0.8-1.2; and further wherein said reactions are conducted in a temperature range of about 0° to 100° C.

2. The process according to claim 1, wherein Ar is m-nitrophenyl or o-nitrophenyl; $R^1$ and $R^2$ together form 1,3-propylene, 1,3-dimethyl-1,3-propylene or 2,2-dimethyl-1,3-propylene; $R^3$ and $R^4$ together form 1,5-pentylene or $-CH_2CH_2OCH_2CH_2-$; each of $R^5$ and $R^6$ is hydrogen or halogen; and X is fluorine or chlorine.

3. The process according to claim 1, which is conducted by the reaction (b), wherein Ar is phenyl substituted by one substituent selected from the group consisting of chlorine, nitro and cyano or by two chlorine atoms; each of $R^1$ and $R^2$ is $C_1-C_4$ alkyl, or $R^1$ and $R^2$ together form 1,3-propylene which is unsubstituted or substituted by from one to four methyl groups; $R^3$ and $R^4$ together form 1,4-butylene, 1,5-pentylene or $-CH_2CH_2OCH_2CH_2-$; each of $R^5$ and $R^6$ is hydrogen or halogen; and X is fluorine or chlorine.

4. The process according to claim 1, wherein the molar ratios of the compounds of the formulas I, II, IV and V are I:II:IV:V being 0.95-1.05:0.95-1.05:0.1-2.0:0-.1-2.0; and the molar ratios of the compounds of the formulas II, V and VI are II:V:VI beng 0.95-1.05:1-.9-2.1:0.95-1.05.

5. The process according to claim 1, wherein said reaction (a) and reaction (b) are each conducted in the presence of a solvent comprising tetrahydrofuran, dimethylformamide, dimethylacetamide, N-methylpyrrolidone, dichloromethane, chloroform, dimethylsulfoxide, acetonitrile, benzene, toluene, xylene or ethyl acetate.

6. The process according to claim 5, wherein said solvent is toluene, benzene, tetrahydrofuran, acetonitrile and chloroform.

7. The process according to claim 6, wherein said solvent is toluene or benzene.

* * * * *